United States Patent [19]　[11]　4,263,458

Bowden et al.　[45]　Apr. 21, 1981

[54] PREPARATION OF AROMATIC FLUORO-COMPOUNDS

[75] Inventors: Roy D. Bowden, Frodsham; Leslie Burgess, Runcorn; Raymond J. Clark, Mossley Hill, all of England

[73] Assignee: Imperial Chemical Industries Limited, London, England

[21] Appl. No.: 22,595

[22] Filed: Mar. 19, 1979

[30] Foreign Application Priority Data

Aug. 25, 1978 [GB] United Kingdom ............... 34662/78

[51] Int. Cl.³ ............................................. C07C 45/28
[52] U.S. Cl. ..................................... 568/323; 568/309
[58] Field of Search ............................ 260/591, 649 F; 568/323, 309

[56] References Cited

U.S. PATENT DOCUMENTS

| 3,479,400 | 11/1969 | Lese et al. ............................ 260/591 |
| 4,022,838 | 5/1977 | Onopchenko et al. ............... 260/591 |
| 4,075,252 | 2/1978 | Boudakian et al. ............... 260/649 F |
| 4,096,196 | 6/1978 | Boudakian et al. ............... 260/649 F |

FOREIGN PATENT DOCUMENTS 53-8133074  7/1978  Japan .................................... 260/649 F

OTHER PUBLICATIONS

Lichtenberger et al., Bull. Soc. Chim. France, pp. 318–325 (1951).
Thorne et al., "Inorganic Chemistry", pp. 675+690–692 (1943).

*Primary Examiner*—James H. Reamer
*Attorney, Agent, or Firm*—Cushman, Darby & Cushman

[57]　ABSTRACT

4,4'-difluoro-benzophenone is prepared from 4,4'-diamino-diphenylmethane by diazotization in anhydrous or concentrated aqueous hydrogen fluoride and decomposition of the diazonium fluoride thus produced in the presence of nitrous acid or nitrite as oxidizing agent.

6 Claims, No Drawings

PREPARATION OF AROMATIC FLUORO-COMPOUNDS

The present invention relates to a process for the preparation of 4,4′-difluorobenzophenone.

4,4′-difluorobenzophenone is a useful monomeric reactant for the production of aromatic polyketone polymers whose molecular chains comprise phenylene groups, oxygen atoms and ketone groups. For example, 4,4′-difluorobenzophenone may be condensed with the di(alkali metal) salts of numerous aromatic bisphenols to form different polyketones as described in British Pat. Nos. 1 078 234 and 1 414 421. Alternatively 4,4′-difluorobenzophenone may be condensed with aromatic bisphenols in the presence of alkali metal carbonates or bicarbonates to form polyketones, as in the process described in Canadian Pat. No. 847 963.

Known methods for the production of 4,4′-difluorobenzophenone involve the use of Friedel Crafts acylations employing fluorobenzene as starting material. Such methods include reacting fluorobenzene with p-fluoro-benzoyl chloride or phosgene. However fluorobenzene is an expensive material and the reaction of fluorobenzene with phosgene produce an isomeric mixture which requires costly purification. Furthermore the handling and disposal of large amounts of spent catalysts (as would be required on a production scale) would also be costly.

The present invention provides a cheaper, easily operable process for the production of 4,4′-difluorobenzophenone without the production of unwanted isomers.

We have found that 4,4′-difluorobenzophenone may be prepared by diazotization of 4,4′-diamino-diphenylmethane in anhydrous or concentrated aqueous hydrogen fluoride and decomposition of the diazonium fluoride thus produced in the presence of nitrous acid or nitrite ions as oxidising agent.

We have found, surprisingly, that when the decomposition of the diazonium fluoride is carried out in the presence of nitrous acid or nitrite ions, oxidation of the methylene group to the carbonyl group of the desired product can be achieved directly, without the need for a subsequent oxidation stage. The reaction mechanism is not fully understood; when the decomposition of the diazonium fluoride is carried out in the presence of nitrous acid or nitrite ions 4,4′-difluoro-diphenylmethane is not necessarily formed as an intermediate (ie fluorination does not necessarily precede oxidation of the methylene group).

Thus according to the present invention there is provided a process for the preparation of 4,4′-difluorobenzophenone which comprises the following steps:

(1) diazotization of 4,4′-diamino-diphenylmethane in anhydrous or concentrated aqueous hydrogen fluoride to yield a solution of a corresponding diazonium fluoride and (2) thermally decomposing the diazonium fluoride in the solution produced in Step 1, in the presence of nitrous acid or nitrite ions as oxidising agent, to yield 4,4′-difluorobenzophenone.

The nature of the ionic species present in anhydrous or concentrated aqueous hydrogen fluoride is not fully understood and the terms "nitrous acid" and "nitrite", as used herein, include species derived from nitrous acid or nitrite ions in the reaction medium, for example HF complexes of $N_2O_3$.

The process is most conveniently carried out by introducing nitrite ions in the form of an alkali metal nitrite, preferably sodium nitrite. The nitrite is preferably introduced in the form of a solution in anhydrous or concentrated aqueous hydrogen fluoride.

In general, the yield of the desired product decreases as the proportion of water in the reaction mixture increases. If desired, anhydrous hydrogen fluoride may be used as the initial medium and as the solvent for the nitrous acid or nitrite introduced. It will be appreciated, however, that water is produced in the overall process leading from 4,4′-diamino-diphenylmethane to 4,4′-difluoro-benzophenone. Accordingly, there is no point in rigorous exlusion of water from the reaction medium but if aqueous hydrogen fluoride is employed as the initial medium this preferably contains at least 60%, preferably at least 70%, by weight of HF. The proportion of water initially present is preferably chosen so that at the end of the process the proportion of water (including that produced in the process) is less than 50% by weight of the total of HF and water; preferably the final proportion of water is less than 40%, particularly less than 30%, on this basis.

From stoichiometric considerations, there should be at least 4 moles of HF present per mole of 4,4′-diamino-diphenylmethane. However since HF is also employed as solvent it is usually present in a large excess over stoichiometric, e.g. in a 5–30 fold excess over the stoichiometrically necessary quantity. A large amount of HF will also minimise (by dilution) the effect of the water produced in the diazotization reaction.

If desired, the diazotization (Step 1) and the decomposition/oxidation (Step 2) may be combined into a single stage by carrying out the diazotization at a temperature of at least 40° C., using an excess of nitrous acid or nitrite over and above the proportion required for the diazotization itself. The proportion of nitrous acid or nitrite employed is preferably at least 3 moles per mole of 4,4′-diamino-diphenylmethane, for example from 4 to 6 moles of nitrous acid or nitrite per mole of 4,4′-diamino-diphenylmethane. A greater excess may be used if desired but in general no benefit is secured by increasing the proportion of nitrous acid or nitrite beyond this range.

Thus Step 1 and Step 2 may be combined by adding the nitrous acid or nitrite continuously or incrementally to a solution of 4,4′-diamino-diphenylmethane in anhydrous or concentrated aqueous hydrogen fluoride maintained at a temperature of at least 40° C., for example in the range from 40° C. to 100° C., the total proportion of nitrous acid and/or nitrite introduced being at least 3 moles per mole of 4,4′-diamino-diphenylmethane; the temperature of the reaction mixture may then be maintained at 40° C. or above for such further period as may be necessary to effect conversion to 4,4′-difluorobenzophenone. In this embodiment of the invention the temperature of the reaction mixture is preferably maintained at 50° C. or above (for example from 50° C. to 100° C., especially from 50° C. to 70° C.) both during the addition of the nitrous acid or nitrite and during any further period of heating.

Alternatively, Step 1 may be followed by Step 2 as a separate stage. Thus the process of diazotization may be carried out at a relatively low temperature, for example at a temperature of 5° C. or below, the reaction mixture subsequently being heated to a temperature of at least 40° C. in the presence of excess nitrous acid or nitrite ions. In this embodiment, the proportion of nitrous acid or nitrite introduced at the relatively low temperature may simply be the stoichiometric proportion required for diazotization (2 moles of nitrous acid or nitrite per mole of 4,4'-diamino-diphenylmethane) or a slight excess over this proportion (for example a 5% excess); the balance of the nitrous acid or nitrite required to provide the total of at least 3 moles per mole may then be introduced when the temperature of the reaction mixture has subsequently been raised to 40° C. or above. If desired, however, all or part of this balance of nitrous acid or nitrite required may be introduced at the relatively low temperature. In this embodiment also, the temperature of the reaction mixture is preferably maintained at 50° C. or above during the heating stage and the total proportion of nitrous acid and/or nitrite introduced is at least 4 moles per mole of 4,4'-diamino-diphenylmethane (for example from 4 to 6 moles per mole).

The time required at the heating stage (Step 2) will depend upon such factors as the concentration of hydrogen fluoride, the excess of nitrous acid or nitrite and the temperature employed. In general the temperature of the reaction mixture will be maintained at 40° C. or above for a period ranging from about half an hour to several hours after addition of the nitrous acid or nitrite has been completed.

The heating stage (Step 2) is conveniently carried out under reflux conditions. The proportion of water at this stage may be increased, if necessary, to allow the required temperature to be maintained under reflux conditions; alternatively, superatmospheric pressure may be used.

After completion of the reaction, 4,4'-difluorobenzophenone may be separated from the reaction mixture by conventional methods, for example solvent extraction.

The invention is illustrated by the following Examples.

EXAMPLE 1

A solution of 4,4'-diamino-diphenylmethane (79.2 g, 0.4 mole) in aqueous 85% w/w hydrogen fluoride (300 g) was prepared in a reactor equipped with a stirrer and condenser.

A solution of sodium nitrite (112.6 g, 1.63 mole) in aqueous 85% w/w hydrogen fluoride (700 g) was prepared at −5° C. The cold nitrite solution was continuously added dropwise over 15 minutes to the solution of 4,4'-diamino-diphenylamine which was initially at −16° C. The reaction mixture was cooled so that the temperature did not rise above 2° C. during addition of the nitrite solution.

After addition of the nitrite solution had been completed, the mixture was heated to reflux temperature (55° C. to 60° C.), maintained under reflux for 2¼ hours and then allowed to cool to room temperature. The reaction mixture was subjected to solvent extraction with diethyl ether, the extract washed with water and the ether removed. The product was recrystallised from an 80/20 weight/weight mixture of industrial methylated spirits and water to yield 35.7 g (41%) of 4,4'-difluorobenzophenone, melting point 108° C. The structure of the product was confirmed by infra-red and nuclear magnetic resonance spectroscopy.

EXAMPLE 2

The general procedure was similar to that described in Example 1.

A solution of sodium nitrite (115 g, 2.24 mole) in aqueous 95% w/w hydrogen fluoride (575 ml) was prepared at −10° C. A portion of this solution (210 ml, 0.815 mole of nitrite) was added rapidly, with stirring, to a solution of 4,4'-diamino-diphenylmethane (79.2 g, 0.40 mole) in aqueous 95% w/w hydrogen fluoride (150 ml), the temperature being maintained between −20° C. and −10° C. This addition effected diazotization; the rest of the nitrite solution was added over a period of 2 hours while the temperature was maintained at −10° C. or below. The mixture was then heated to reflux (55° C. to 57° C.) over a period of 45 minutes and maintained under reflux for 3 hours.

After cooling to room temperature, the reaction mixture was extracted with three 200 ml portions of carbon tetrachloride. The combined extracts were washed with water and the solvent was removed by distillation. The product was recrystallised from an 80/20 w/w mixture of industrial methylated spirits/water to yield 68.5 g (78%) of 4,4'-difluorobenzophenone (melting point 108° C.).

EXAMPLE 3

The general procedure was similar to that described in Example 1.

Solid sodium nitrite (127 g, 1.84 mole) was added slowly, with stirring, to a solution of 4,4'-diamino-diphenylmethane (79.2 g, 0.40 mole) in aqueous 90% w/w hydrogen fluoride (590 g), the temperature being maintained between −20° C. and −10° C. The mixture was then heated to reflux (62° C. to 64° C.) over a period of 1.5 hours and maintained under reflux for 1 hour.

After cooling to room temperature, the reaction mixture was extracted with three 200 ml portions of carbon tetrachloride. The product was extracted and recrystallised (as described in Example 3) to yield 53.5 g (61%) of 4,4'-difluorobenzophenone (melting point 108° C.).

What is claimed is:

1. A process for the preparation of 4,4'-difluoro-benzophenone which comprises the following steps:
   (1) diazotization of 4,4'-diamino-diphenylmethane in anhydrous or concentrated aqueous hydrogen fluoride to yield a solution of a corresponding diazonium fluoride and
   (2) thermally decomposing the diazonium fluoride in the solution produced in Step 1, in the presence of nitrous acid or nitrite ions as oxidising agent, to yield 4,4'-difluorobenzophenone.

2. A process according to claim 1 characterised in that the diazotization (Step 1) is carried out using sodium nitrite introduced in the form of a solution in anhydrous or concentrated aqueous hydrogen fluoride.

3. A process according to claim 1 or claim 2 wherein the diazotization (Step 1) is followed by Step 2 and wherein Step 2 is carried out at a temperature in the range from 40° C. to 100° C.

4. A process according to claim 3 wherein Step 2 is carried out at a temperature in the range from 50° C. to 70° C.

5. A process according to claim 1 or claim 2 wherein the diazotization (Step 1) is combined with Step 2 by adding nitrous acid or nitrite continuously or incrementally over at least part of the total reaction period to a solution of 4,4'-diamino-diphenylmethane in anhydrous or concentrated aqueous hydrogen fluoride maintained at a temperature in the range from 40° C. to 100° C.

6. A process according to claim 5 wherein the temperature is in the range from 50° C. to 70° C.

* * * * *